United States Patent
Nguyen et al.

(10) Patent No.: US 11,389,641 B2
(45) Date of Patent: Jul. 19, 2022

(54) MODULAR FLYING LEAD CABLE AND METHODS FOR USE WITH HEART PUMP CONTROLLERS

(71) Applicant: TC1 LLC, St. Paul, MN (US)

(72) Inventors: John Nguyen, San Ramon, CA (US); Fabian Franco, Livermore, CA (US); Mark Di Paola, Livermore, CA (US); Carine Hoarau, Pleasant Hill, CA (US); Nathan Harold, Pleasanton, CA (US); Michael Morado, Escalan, CA (US)

(73) Assignee: TC1 LLC, St. Paul, MN (US)

( * ) Notice: Subject to any disclaimer, the term of this patent is extended or adjusted under 35 U.S.C. 154(b) by 98 days.

(21) Appl. No.: 16/359,925

(22) Filed: Mar. 20, 2019

(65) Prior Publication Data
US 2019/0290820 A1    Sep. 26, 2019

Related U.S. Application Data

(60) Provisional application No. 62/646,174, filed on Mar. 21, 2018.

(51) Int. Cl.
*A61M 60/871* (2021.01)
*A61N 1/378* (2006.01)
(Continued)

(52) U.S. Cl.
CPC ........ *A61M 60/871* (2021.01); *A61M 60/148* (2021.01); *A61N 1/3787* (2013.01);
(Continued)

(58) Field of Classification Search
CPC .... A61M 1/127; A61M 1/122; A61M 1/3787; A61M 1/1086; A61M 1/3627; A61M 1/3752
(Continued)

(56) References Cited

U.S. PATENT DOCUMENTS

| | | |
|---|---|---|
| 3,882,861 A | 5/1975 | Kettering et al. |
| 4,521,871 A | 6/1985 | Galdun et al. |
| 5,046,965 A | 9/1991 | Neese et al. |
| 5,695,474 A | 12/1997 | Daugherty |

(Continued)

FOREIGN PATENT DOCUMENTS

| | | |
|---|---|---|
| EP | 1 812 094 A | 5/2006 |
| WO | 2006055745 A2 | 5/2006 |

(Continued)

OTHER PUBLICATIONS

Heartmate II, "The HeartMate II System", HeartMate II, Left Ventricular Assist System, Retrieved from Internet: http://heartmateii.com/heartmate-ii-system.aspx, Jul. 16, 2015, 2 pages.

(Continued)

*Primary Examiner* — Carl H Layno
*Assistant Examiner* — Michael J Lau
(74) *Attorney, Agent, or Firm* — Kilpatrick Townsend & Stockton LLP

(57) ABSTRACT

An external controller assembly for a medical device implanted in a patient includes an external controller and an external driveline assembly. The external controller includes an external controller display viewable by the patient. The external driveline assembly includes an external driveline cable and an external driveline distal connector. The external driveline cable is connected to the external driveline distal connector and the external controller. The external driveline cable accommodates positioning of the external driveline distal connector, by the patient, for simultaneous viewing of the external driveline distal connector and the external controller display by the patient. The external driveline distal connector is adapted to be connected to the distal driveline proximal connector by the patient. The external
(Continued)

driveline distal connector is adapted to be disconnected from the distal driveline proximal connector by the patient.

20 Claims, 5 Drawing Sheets

(51) Int. Cl.
*A61M 60/148* (2021.01)
*A61N 1/375* (2006.01)
*A61N 1/362* (2006.01)
*A61M 60/50* (2021.01)

(52) U.S. Cl.
CPC ............ *A61M 60/50* (2021.01); *A61N 1/3627* (2013.01); *A61N 1/3752* (2013.01)

(58) Field of Classification Search
USPC .......................................................... 600/16
See application file for complete search history.

(56) References Cited

U.S. PATENT DOCUMENTS

| | | | |
|---|---|---|---|
| 5,853,394 A * | 12/1998 | Tolkoff | A61M 39/0208 604/288.01 |
| 5,888,242 A | 3/1999 | Antaki et al. | |
| 5,904,646 A * | 5/1999 | Jarvik | A61M 39/0247 600/16 |
| 5,935,105 A | 8/1999 | Manning et al. | |
| 5,991,595 A | 11/1999 | Romano et al. | |
| 6,004,269 A * | 12/1999 | Crowley | A61B 8/4461 600/374 |
| 6,071,093 A | 6/2000 | Hart | |
| 6,116,862 A | 9/2000 | Rau et al. | |
| 6,123,726 A * | 9/2000 | Mori | A61M 60/829 623/3.27 |
| 6,146,179 A | 11/2000 | Denny et al. | |
| 6,183,412 B1 | 2/2001 | Benkowski et al. | |
| 6,234,772 B1 | 5/2001 | Wampler et al. | |
| 6,264,635 B1 | 7/2001 | Wampler et al. | |
| 6,305,962 B1 | 10/2001 | Maher et al. | |
| 6,494,736 B2 | 12/2002 | Mito | |
| 6,508,756 B1 * | 1/2003 | Kung | A61M 60/869 600/37 |
| 6,592,620 B1 | 7/2003 | Lancisi et al. | |
| 6,688,861 B2 | 2/2004 | Wampler | |
| 7,340,304 B2 | 3/2008 | MacDonald et al. | |
| 7,425,142 B1 | 9/2008 | Putz | |
| 7,658,613 B1 | 2/2010 | Griffin et al. | |
| 7,699,586 B2 | 4/2010 | LaRose et al. | |
| 7,771,221 B1 * | 8/2010 | Blackwell | H01R 13/52 439/282 |
| 7,961,156 B2 | 6/2011 | Knott et al. | |
| 7,976,271 B2 | 7/2011 | LaRose et al. | |
| 7,997,854 B2 | 8/2011 | LaRose et al. | |
| 8,007,254 B2 | 8/2011 | LaRose et al. | |
| 8,029,441 B2 | 10/2011 | Mazza et al. | |
| 8,152,493 B2 | 4/2012 | LaRose et al. | |
| 8,157,720 B2 | 4/2012 | Marseille et al. | |
| 8,186,665 B2 | 5/2012 | Akema | |
| 8,323,174 B2 | 12/2012 | Jeevanandam et al. | |
| 8,344,847 B2 | 1/2013 | Moberg et al. | |
| 8,348,678 B2 | 1/2013 | Hardisty et al. | |
| 8,449,444 B2 | 5/2013 | Poirier | |
| 8,500,620 B2 * | 8/2013 | Lu | A61M 60/268 600/16 |
| 8,506,471 B2 | 8/2013 | Bourque | |
| 8,562,508 B2 | 10/2013 | Dague et al. | |
| 8,597,350 B2 | 12/2013 | Rudser et al. | |
| 8,628,460 B2 | 1/2014 | Yomtov et al. | |
| 8,639,348 B2 | 1/2014 | Geheb | |
| 8,652,024 B1 * | 2/2014 | Yanai | A61M 39/1011 600/16 |
| 8,657,733 B2 | 2/2014 | Ayre et al. | |
| 8,668,473 B2 | 3/2014 | LaRose et al. | |
| 8,684,763 B2 | 4/2014 | Mattson et al. | |
| 8,794,989 B2 | 8/2014 | Kearsley et al. | |
| 8,894,561 B2 | 11/2014 | Callaway et al. | |
| 8,971,958 B2 | 3/2015 | Frikart et al. | |
| 9,302,035 B2 | 4/2016 | Marseille et al. | |
| 9,452,249 B2 | 9/2016 | Kearsley et al. | |
| 9,985,374 B2 | 5/2018 | Hodges | |
| 10,124,101 B2 | 11/2018 | Wong et al. | |
| 2002/0007198 A1 | 1/2002 | Haupert et al. | |
| 2005/0055038 A1 * | 3/2005 | Kelleher | A61B 17/072 606/151 |
| 2005/0069426 A1 * | 3/2005 | Mason | C12M 29/12 417/394 |
| 2005/0071001 A1 | 3/2005 | Jarvik | |
| 2006/0226423 A1 * | 10/2006 | Yamasaki | G02F 1/136213 257/59 |
| 2007/0078293 A1 | 4/2007 | Shambaugh, Jr. et al. | |
| 2007/0142696 A1 | 6/2007 | Crosby et al. | |
| 2007/0208290 A1 * | 9/2007 | Pecor | A61M 39/1011 604/4.01 |
| 2008/0021394 A1 | 1/2008 | LaRose et al. | |
| 2009/0118827 A1 | 5/2009 | Sugiura | |
| 2009/0203957 A1 | 8/2009 | LaRose et al. | |
| 2010/0305692 A1 * | 12/2010 | Thomas | A61M 60/148 623/3.1 |
| 2011/0071336 A1 * | 3/2011 | Yomtov | A61M 60/871 600/16 |
| 2011/0160516 A1 | 6/2011 | Dague et al. | |
| 2011/0196189 A1 * | 8/2011 | Milbocker | A61M 60/40 600/16 |
| 2011/0218383 A1 | 9/2011 | Broen et al. | |
| 2011/0270331 A1 * | 11/2011 | Peters | A61M 60/135 607/3 |
| 2012/0028490 A1 * | 2/2012 | Litzler | H01R 31/02 439/278 |
| 2012/0046514 A1 | 2/2012 | Bourque | |
| 2012/0095281 A1 | 4/2012 | Reichenbach et al. | |
| 2012/0149229 A1 * | 6/2012 | Kearsley | A61M 60/871 439/339 |
| 2012/0172657 A1 | 7/2012 | Marseille et al. | |
| 2012/0183261 A1 | 7/2012 | Schwandt et al. | |
| 2013/0096364 A1 | 4/2013 | Reichenbach et al. | |
| 2013/0121821 A1 | 5/2013 | Ozaki et al. | |
| 2013/0127253 A1 | 5/2013 | Stark et al. | |
| 2013/0170970 A1 | 7/2013 | Ozaki et al. | |
| 2013/0225909 A1 | 8/2013 | Dormanen et al. | |
| 2013/0310631 A1 * | 11/2013 | Lee | G08C 23/04 600/16 |
| 2013/0314047 A1 | 11/2013 | Eagle et al. | |
| 2014/0073838 A1 | 3/2014 | Dague et al. | |
| 2014/0094645 A1 * | 4/2014 | Lafontaine | A61M 60/00 600/16 |
| 2014/0188148 A1 * | 7/2014 | le Blanc | A61B 17/320016 606/181 |
| 2014/0194670 A1 * | 7/2014 | Wildhirt | A61N 1/0587 600/16 |
| 2014/0194985 A1 | 7/2014 | Vadala, Jr. | |
| 2014/0243970 A1 | 8/2014 | Yanai | |
| 2014/0309733 A1 | 10/2014 | Cotter et al. | |
| 2015/0031937 A1 * | 1/2015 | Kearsley | H01B 7/048 600/16 |
| 2015/0038771 A1 | 2/2015 | Marseille et al. | |
| 2015/0290377 A1 * | 10/2015 | Kearsley | A61M 60/148 49/465 |
| 2015/0367047 A1 * | 12/2015 | Vadala, Jr. | G06F 1/263 600/16 |
| 2016/0064117 A1 * | 3/2016 | Romero | H01B 7/048 600/16 |
| 2016/0095968 A1 | 4/2016 | Rudser | |
| 2016/0175502 A1 * | 6/2016 | McSweeney | A61M 60/857 623/3.26 |
| 2016/0181730 A1 * | 6/2016 | Eldridge | A61M 60/122 600/16 |
| 2017/0173238 A1 * | 6/2017 | Godshall | A61M 60/419 |
| 2017/0324185 A1 * | 11/2017 | Hodges | H01R 43/26 |
| 2017/0354772 A1 * | 12/2017 | Tajima | A61M 60/871 |

(56) References Cited

U.S. PATENT DOCUMENTS

| | | |
|---|---|---|
| 2018/0001007 A1* | 1/2018 | Stratton .............. A61M 60/871 |
| 2018/0055983 A1* | 3/2018 | Bourque ............. A61F 2/30744 |
| 2018/0250459 A1 | 9/2018 | Kimball et al. |
| 2018/0256796 A1 | 9/2018 | Hansen |
| 2018/0256800 A1 | 9/2018 | Conyers et al. |
| 2018/0256801 A1 | 9/2018 | Conyers et al. |

FOREIGN PATENT DOCUMENTS

| | | |
|---|---|---|
| WO | 2010122139 A1 | 10/2010 |
| WO | 2011081626 A1 | 7/2011 |
| WO | 2014107424 A2 | 7/2014 |
| WO | 2015017770 A1 | 2/2015 |
| WO | 2017087380 A1 | 5/2017 |

OTHER PUBLICATIONS

My Lvad, "Berlin Heart Incor", Retrieved from Internet:http://www.mylvad.com/content/berlin-heart-incor, Jul. 16, 2015, 3 pages.
Di Paola et al., "Improved Blood Pump Connectors", U.S. Appl. No. 16/395,134, filed Apr. 25, 2019, Unpublished, 94 pages.

* cited by examiner

MODULAR FLYING LEAD CABLE AND METHODS FOR USE WITH HEART PUMP CONTROLLERS

CROSS REFERENCE TO RELATED APPLICATIONS

The present application claims the benefit under 35 USC § 119(e) of US Provisional Appln. No. 62/646,174 filed Mar. 21, 2018; the full disclosure which is incorporated herein by reference in its entirety for all purposes.

BACKGROUND

Ventricular assist devices, known as VADs, often include an implantable blood pump and are used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries and/or high blood pressure can leave a heart too weak to pump enough blood to the body. As symptoms worsen, advanced heart failure develops.

A patient suffering from heart failure may use a VAD while awaiting a heart transplant or as a long term therapy. A patient may also use a VAD while recovering from heart surgery. Thus, a VAD can supplement a weak heart (i.e., partial support) or can effectively replace the natural heart's function.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

In embodiments described herein, an external controller assembly for an implanted medical device (e.g., a implanted blood pump) includes an external controller and an external driveline assembly connected to, and extending from, the external controller. The external driveline assembly includes an external driveline distal connector and an external driveline cable extending between the external controller and the external driveline distal connector. In many embodiments, the external driveline distal connector is adapted so that a patient in which the medical device is implanted can (a) connect the external controller assembly to a distal driveline assembly that is connected to the implanted medical device, and (b) disconnect the external controller assembly from the distal driveline assembly. In many embodiments, the external driveline cable has a length and flexibility that enables the patient to position and orient the external driveline distal connector to more easily align and connect the external driveline distal connector with a distal driveline proximal connector of the distal driveline assembly. In many embodiments, the length and flexibility of the external driveline cable enables the patient to position and orient the external driveline distal connector to more easily disconnect the external driveline distal connector from the distal driveline proximal connector. For example, in many embodiments, the external driveline assembly enables the patient to position and orient the external driveline distal connector to directly observe the angular orientation of the external driveline distal connector relative to an insertion axis of the external driveline distal connector. In many embodiments, the external driveline assembly enables the patient to hold the external driveline distal connector in one hand and hold the distal driveline proximal connector in the other hand in positions and orientations that best enable the patient to make the connection or the disconnection. For example, in many embodiments, the external driveline assembly enables the patient to position the external driveline distal connector and the distal driveline proximal connector out in front of the patient while the external controller is disposed in a holder attached to a support belt worn by the patient, thereby enabling the patient to directly observe the connection and disconnection and apply sufficient force to make the connection or the disconnection.

Thus, in one aspect, a blood circulation assist system includes an implantable blood pump, an external controller, a distal driveline assembly, and an external driveline assembly. Power to operate the implantable blood pump is supplied to the implantable blood pump via the external controller. The external controller includes an external controller display viewable by a patient in which the implantable blood pump is implanted. The distal driveline assembly includes a percutaneous cable connected to the implantable blood pump and a distal driveline proximal connector electrically coupled with the percutaneous cable. The percutaneous cable has a skin-interface segment adapted to extend through a skin of the patient. The external driveline assembly includes an external driveline cable and an external driveline distal connector. The external driveline cable is connected to the external driveline distal connector and the external controller. The external driveline cable accommodates positioning of the external driveline distal connector, by the patient, for simultaneous viewing of the external driveline distal connector and the external controller display by the patient. The external driveline distal connector is adapted to be connected to the distal driveline proximal connector by the patient. The external driveline distal connector is adapted to be disconnected from the distal driveline proximal connector by the patient.

In many embodiments of the blood circulation assist system, the external driveline cable has a length and a flexibility that enables the patient to position and/or orient the external driveline distal connector to facilitate connection, by the patient, of the external driveline distal connector to the distal driveline proximal connector and disconnection, by the patient, of the external driveline distal connector from the distal driveline proximal connector. For example, in some embodiments, the external driveline cable has a length and a flexibility to accommodate the positioning of the external driveline distal connector, by the patient, for simultaneous viewing of the external driveline distal connector and the external controller display by the patient. In some embodiments, the length of the external driveline cable is from 5 inches to 9 inches.

In some embodiments of the blood circulation assist system, the external driveline assembly is connected to the external controller so as to prevent disconnection of the external driveline assembly from the external controller without the use of a tool. For example, in some embodiments: (a) the external controller includes an external driveline connection port, (b) the external driveline assembly includes an external driveline proximal connector by which the external driveline cable is connected to the external driveline connection port; and (c) the external controller includes an external driveline latching mechanism that prevents the patient from disconnecting the external driveline proximal connector from the external driveline connection port without the use of a tool (e.g., a key, a specialized tool).

In some embodiments of the blood circulation assist system, the external controller and the external driveline assembly are adapted to detect whether the external driveline assembly is connected to the distal driveline assembly. For example, in some embodiments: (a) the external driveline assembly includes a first connection lead and a second connection lead, (b) the second connection lead is electrically connected to the first connection lead while the external driveline distal connector is connected to the distal driveline proximal connector, (c) the second connection lead is electrically disconnected from the first connection lead while the external driveline distal connector is not connected to the distal driveline proximal connector, and (d) the external controller detects whether the external driveline distal connector is connected to the distal driveline proximal connector by detecting whether the second connection lead is electrically connected to the first connection lead.

In many embodiments of the blood circulation assist system, the distal driveline assembly includes a percutaneous driveline assembly and an intermediate driveline assembly. In such embodiments, the intermediate driveline assembly can include the distal driveline proximal connector, an intermediate driveline cable, and an intermediate driveline distal connector. The intermediate driveline cable connects the distal driveline proximal connector to the intermediate driveline distal connector. In such embodiments, the percutaneous driveline assembly can include a percutaneous driveline proximal connector and the percutaneous cable. The percutaneous driveline proximal connector is connectable to the intermediate driveline distal connector. In many embodiments, the percutaneous driveline proximal connector and the intermediate driveline distal connector are adapted to be connected so that the patient cannot disconnect the intermediate driveline distal connector and the percutaneous driveline proximal connector by hand. For example, in some embodiments, the blood circulation assist system includes an intermediate driveline latching mechanism that prevents disconnection of the percutaneous driveline proximal connector and the intermediate driveline distal connector without the use of a tool, which in some embodiments is a specialized tool. In some embodiments, the distal driveline assembly has a flexibility and an exterior length from the skin-interface segment to the distal driveline proximal connector that accommodates positioning of the distal driveline proximal connector, by the patient, between the external controller display and an eye of the patient. In some embodiments, the exterior length of the distal driveline assembly is from 3 inches to 7 inches.

In another aspect, a method of connecting an external controller to a blood pump implanted in a patient is provided. The method includes connecting a distal end of a percutaneous driveline assembly to the blood pump. The percutaneous driveline assembly includes a percutaneous driveline cable and a percutaneous driveline proximal connector. The percutaneous driveline cable extends between the blood pump and the percutaneous driveline proximal connector. The percutaneous driveline cable has a skin-interface segment that extends through a skin of the patient. The method further includes connecting an intermediate driveline assembly to the percutaneous driveline assembly by connecting an intermediate driveline distal connector of the intermediate driveline assembly to the percutaneous driveline proximal connector. The intermediate driveline assembly includes an intermediate driveline proximal connector and an intermediate driveline cable connecting the intermediate driveline distal connector and the intermediate driveline proximal connector. The method further includes connecting an external controller assembly to the intermediate driveline assembly. The external controller assembly includes an external driveline assembly and an external controller via which power is supplied to the blood pump. The external driveline assembly includes an external driveline cable and an external driveline distal connector. The external driveline cable connects the external driveline distal connector with the external controller. The external controller includes an external controller display viewable by the patient. The external driveline cable accommodates positioning of the external driveline distal connector, by the patient, for simultaneous viewing of the external driveline distal connector and the external controller display by the patient.

In many embodiments of the method, the external driveline assembly is secured to the external controller and/or the intermediate driveline assembly is secured to the percutaneous driveline assembly so as to prevent disconnection without the use of a tool (e.g., a key, a specialized tool). For example, in some embodiments, the method further includes securing the intermediate driveline distal connector to the percutaneous driveline proximal connector so as to prevent the patient from disconnecting the intermediate driveline distal connector from the percutaneous driveline proximal connector without the use of a tool, which in some embodiments is a specialized tool. In some embodiments, the method further includes: (a) connecting the external driveline assembly to the external controller by connecting an external driveline proximal connector of the external driveline assembly to an external driveline connection port of the external controller, and (b) securing the external driveline proximal connector to the external driveline connection port so as to prevent the patient from disconnecting the external driveline proximal connector from the external driveline connection port without the use of a tool (e.g., a key, a specialized tool).

In many embodiments of the method, the external driveline cable has a length and a flexibility that enables the patient to position and/or orient the external driveline distal connector to facilitate connection, by the patient, of the external driveline distal connector to the intermediate driveline proximal connector and disconnection, by the patient, of the external driveline distal connector from the intermediate driveline proximal connector. For example, in some embodiments, the external driveline cable has a length and a flexibility to accommodate the positioning of the external driveline distal connector, by the patient, for simultaneous viewing of the external driveline distal connector and the external controller display by the patient. In some embodiments of the method, the length of the external driveline cable is from 5 inches to 9 inches.

In another aspect, an external controller assembly for an implanted blood pump assembly includes an external controller and an external driveline assembly. Power can be supplied to the implantable blood pump via the external controller. The external controller includes an external controller display viewable by the patient. The external driveline assembly includes external driveline cable and an external driveline distal connector. The external driveline cable is connected to the external driveline distal connector and the external controller. The external driveline cable accommodates positioning of the external driveline distal connector, by the patient, for simultaneous viewing of the external driveline distal connector and the external controller display by the patient. The external driveline distal connector is adapted to be connected to a distal driveline proximal connector of a distal driveline assembly by the patient. The external driveline distal connector is adapted to be disconnected from the distal driveline proximal connector by the patient.

In many embodiments of the external controller assembly, the external driveline cable has a length and a flexibility to accommodate the positioning of the external driveline distal connector, by the patient, for simultaneous viewing of the external driveline distal connector and the external controller display by the patient. In some embodiments, the length of the external driveline cable is from 5 inches to 9 inches.

In some embodiments of the external controller assembly, the external driveline is connected to the external controller so as to prevent disconnection of the external driveline from the external controller without the use of a tool. For example, in some embodiments: (a) the external controller includes an external driveline connection port, (b) the external driveline assembly includes an external driveline proximal connector by which the external driveline cable is connected to the external driveline connection port; and (c) the external controller includes an external driveline latching mechanism that prevents the patient from disconnecting the external driveline proximal connector from the external driveline connection port without the use of a tool (e.g., a key, a specialized tool).

In some embodiments of the external controller assembly, the external controller and the external driveline assembly are adapted to detect whether the external driveline assembly is connected to the distal driveline assembly. For example, in some embodiments: (a) the external driveline assembly includes a first connection lead and a second connection lead, (b) the second connection lead is electrically connected to the first connection lead while the external driveline distal connector is connected to the distal driveline proximal connector, (c) the second connection lead is electrically disconnected from the first connection lead while the external driveline distal connector is not connected to the distal driveline proximal connector, and (d) the external controller detects whether the external driveline distal connector is connected to the distal driveline proximal connector by detecting whether the second connection lead is electrically connected to the first connection lead.

For a fuller understanding of the nature and advantages of the present invention, reference should be made to the ensuing detailed description and accompanying drawings.

DETAILED DESCRIPTION

Figure 1:
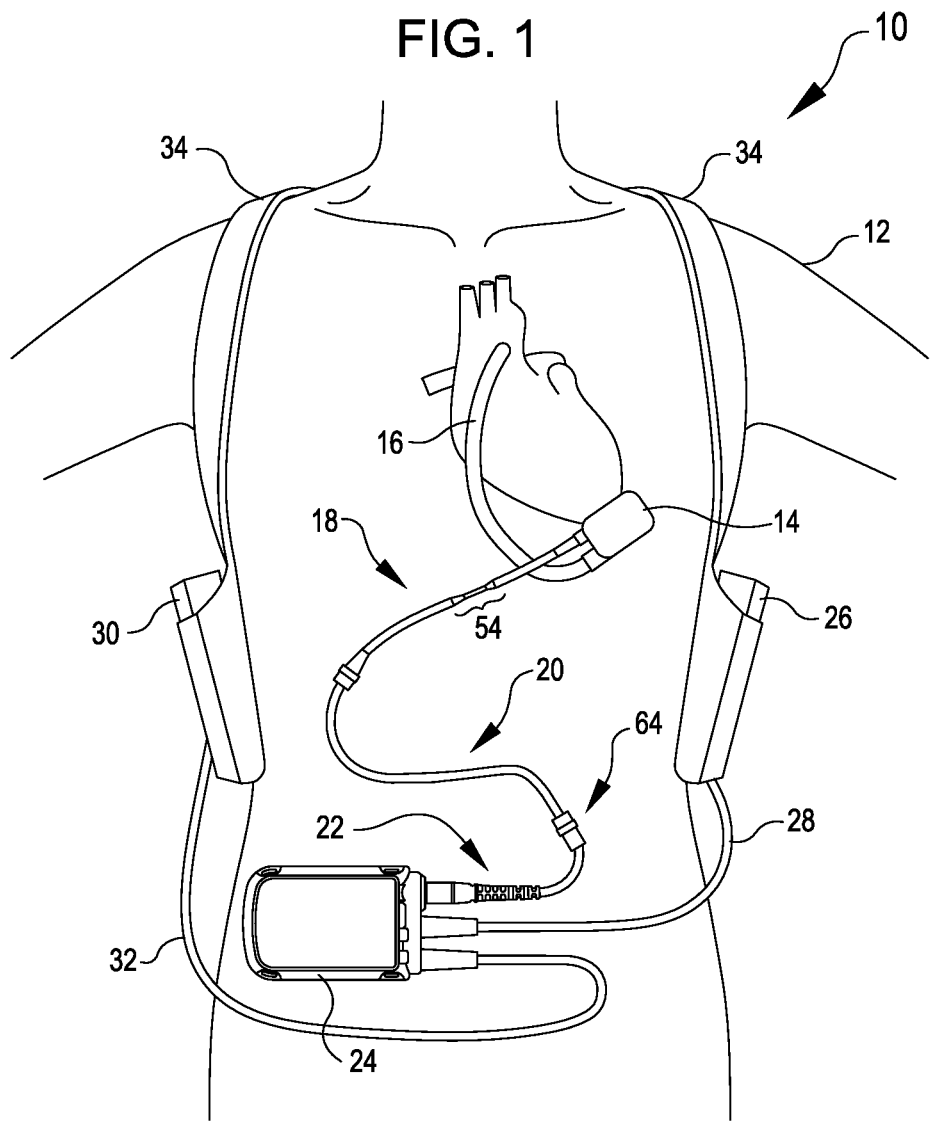
FIG. 1 illustrates a blood circulation assist system that includes an external controller assembly including an external controller and an external driveline assembly connected to, and extending from, the external controller, in accordance with many embodiments.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Embodiments described herein are directed to improving the ability of a patient to reliably and effectively connect an external controller to a driveline assembly connected to an implanted medical device (e.g., an implanted blood pump). In contrast to embodiments described herein, some existing external controllers are difficult to connect to a driveline assembly connected to an implanted medical device. For example, some existing external controllers have a display and a connection port for the driveline assembly that is positioned and oriented so the patient cannot simultaneously view the display and the connection port, thereby preventing the patient from monitoring the display while viewing the connection port. In such existing external controllers, the location and orientation of the connection port contributes to poor ergonomics when attempting to align a proximal connector of the driveline assembly with the connection port during connection of the driveline assembly to the external controller. Moreover, in such existing controllers, a relatively high connection force may be required to connect the proximal connector of the driveline assembly to the connection port of the external controller.

Embodiments described herein include and/or employ an external controller assembly that includes an external controller and an external driveline assembly connected to, and extending from, the external controller. The external driveline assembly includes an external driveline distal connector and an external driveline cable by which the external driveline distal connector is connected to the external controller and by which the external driveline distal connector is disposed at a distance from the external controller. The external driveline assembly moves the patient interaction area away from the external controller. Moving the patient interaction area away from the external controller enables the patient to connect the external driveline distal connector to the proximal connector of the driveline assembly while simultaneously observing the connection and directly monitoring a display of the external controller for a displayed indication that the connection is complete. In many embodiments, the external driveline assembly allows the patient to comfortably grasp the external driveline distal connector in one hand and the proximal connector of the driveline assembly in the other hand while making the connection between the external driveline distal connector and the proximal connector of the distal driveline assembly. In many embodiments, connection of the external driveline distal connector and the proximal connector of the distal driveline assembly can be made using a suitable insertion force that can be generated by most patients. In some embodiments, the external driveline assembly is compatible with existing external controllers.

In many embodiments, the external driveline assembly is pseudo-permanently attached to a connection port of the external controller. The connection of the external driveline assembly to the connection port of the external controller can be made during manufacture of the external controller assembly and/or by a trained technician.

Referring now to the drawings, in which like reference numerals represent like parts throughout the several views, FIG. 1 illustrates a blood circulation assist system 10 being used by a patient 12, in accordance with many embodiments. The blood circulation assist system 10 includes an implantable blood pump 14, a blood flow conduit 16, a percutaneous driveline assembly 18, an intermediate driveline assembly 20, an external driveline assembly 22, an external controller 24, a first battery 26, a first battery cable 28, a second battery 30, a second battery cable 32, and a support harness 34. The support harness 34 has receptacles that hold the first battery 26 and the second battery 30. In many embodiments, the external controller 24 is mountable to the support harness 34 to hold the external controller 24 in a suitable position and orientation relative to the patient 12, such as the position and orientation of the external controller 24 relative to the patient 12 illustrated in FIG. 1.

In a regular operation mode, the blood pump 14 is powered via electrical power supplied by the first battery 26 via the first battery cable 28 and/or by the second battery 30 via the second battery cable 32. Electrical power supplied by the first battery 26 and/or the second battery 30 is transmitted, via the external controller 24, over the external driveline assembly 22, the intermediate driveline assembly 20, and the percutaneous driveline assembly 18 to the blood pump 14. In the illustrated embodiment, the blood pump 14 is a left ventricle assist device (LVAD) that pumps blood from the left ventricle of the patient 12 to the aorta of the patient 12 via the blood flow conduit 16.

The external driveline assembly 22 can be used in connection with any suitable implanted medical device. In the illustrated embodiment, the blood pump 14 is a left ventricle assist device (LVAD) that pumps blood from the left ventricle of the patient 12 to the aorta of the patient 12 via the blood flow conduit 16. In many embodiments, the external driveline assembly 22 is connectable, by the patient 12, to the intermediate driveline assembly 20 via a patient-operable connection assembly 64. In many embodiments, the external driveline assembly 22 can be disconnected, by the patient 12, from the intermediate driveline assembly 20 via the patient-operable connection assembly 64.

Figure 2:
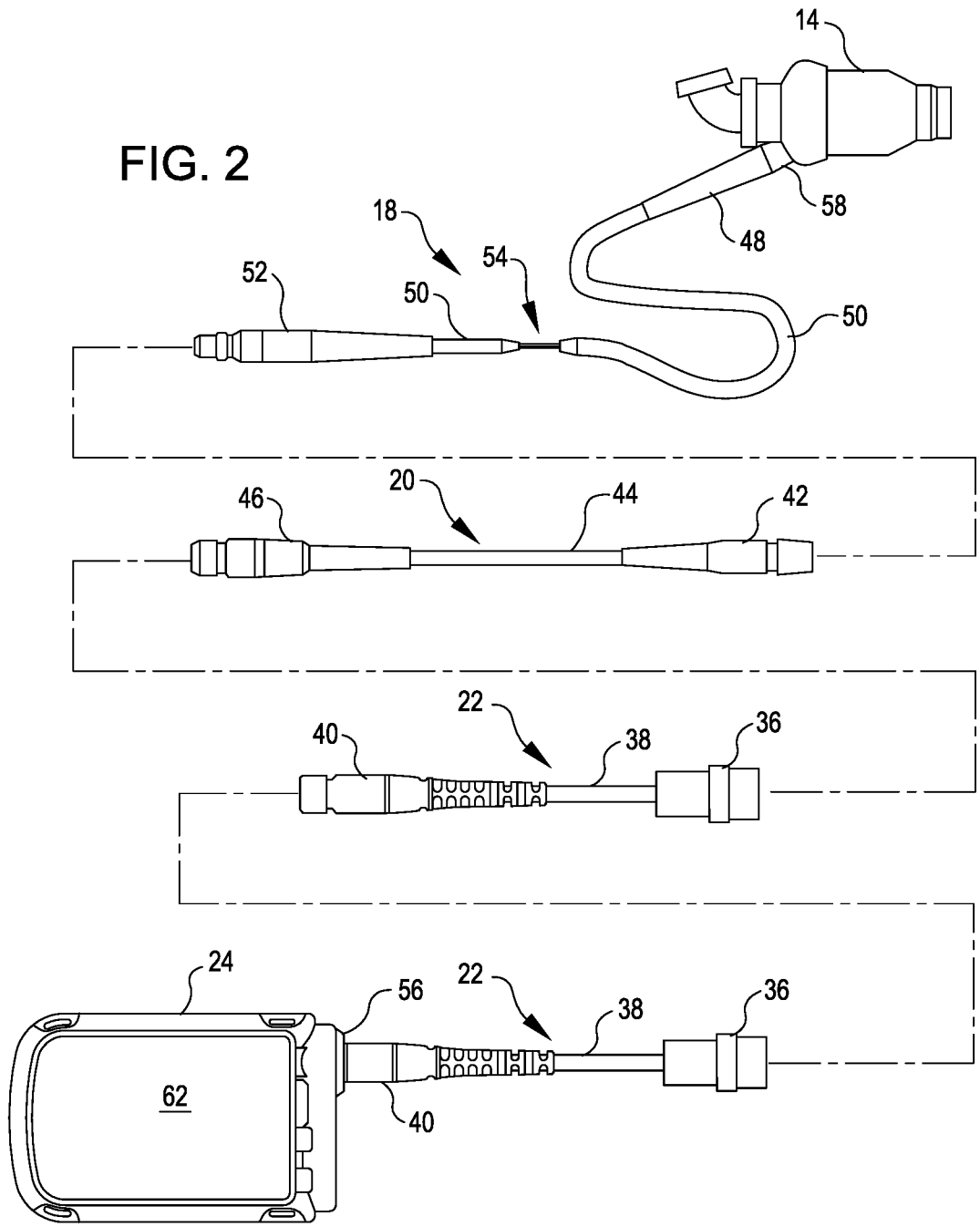
FIG. 2 is an exploded view illustrating driveline assemblies of the blood circulation assist system of FIG. 1.

FIG. 2 is an exploded view illustrating connection of the external controller 24 to the blood pump 14 via the combination of the percutaneous driveline assembly 18, the intermediate driveline assembly 20, and the external driveline assembly 22. The external driveline assembly 22 includes an external driveline distal connector 36, an external driveline cable 38, and an external driveline proximal connector 40. The intermediate driveline assembly 20 includes an intermediate driveline distal connector 42, an intermediate driveline cable 44, and an intermediate driveline proximal connector 46. The percutaneous driveline assembly 18 includes a percutaneous driveline distal connector 48, a percutaneous driveline cable 50, and a percutaneous driveline proximal connector 52. The percutaneous driveline cable 50 includes a skin-interface portion 54. The external controller 24 includes an external driveline connection port 56. The blood pump 14 includes a percutaneous driveline connector 58. The external driveline assembly 22 is connectable to the external controller 24 via insertion of the external driveline proximal connector 40 into the external driveline connection port 56. The external driveline assembly 22 is connectable to the intermediate driveline assembly 20 via connection of the external driveline distal connector 36 and the intermediate driveline proximal connector 46. The intermediate driveline assembly 20 is connectable to the percutaneous driveline assembly 18 via connection of the intermediate driveline distal connector 42 and the percutaneous driveline proximal connector 52. The percutaneous driveline assembly 18 is connected to the blood pump 14 via connection of the percutaneous driveline distal connector 48 and the percutaneous driveline connector 58.

In many embodiments, the external controller 24 includes an external driveline latch mechanism that can be reconfigured between a connection configuration that accommodates connection of the external driveline proximal connector 40 to the external driveline connection port 56 and a retention configuration that blocks disconnection of the external driveline proximal connector 40 from the external driveline connection port 56. In some embodiments, reconfiguration of the external driveline latch mechanism between the connection configuration and the retention configuration requires the use of a tool (e.g., a key, a specialized tool). For example, the external driveline latch mechanism can include a key-operated locking mechanism operable to lock the external driveline latch mechanism in the retention configuration and requiring the use of a key to reconfigure the external driveline latch mechanism from the retention configuration to the connection configuration. In some embodiments, reconfiguration of the external driveline latch mechanism between the connection configuration and the retention configuration does not require the use of a tool (e.g., a key, a specialized tool).

In some embodiments, the connection between the intermediate driveline assembly 20 and the percutaneous driveline assembly 18 prevents disconnection of the intermediate driveline distal connector 42 and the percutaneous driveline proximal connector 52 without the use of a tool (e.g., a specialized tool not typically possessed by the patient). For example, the connection between the intermediate driveline distal connector 42 and the percutaneous driveline proximal connector 52 can be secured via a retainer ring that prevents disconnection without removal of the retainer ring via the use of a retainer ring plier. In some embodiments, the connection between the intermediate driveline assembly 20 and the percutaneous driveline assembly 18 accommodates disconnection of the intermediate driveline distal connector 42 and the percutaneous driveline proximal connector 52 without the use of a tool.

Figure 3:
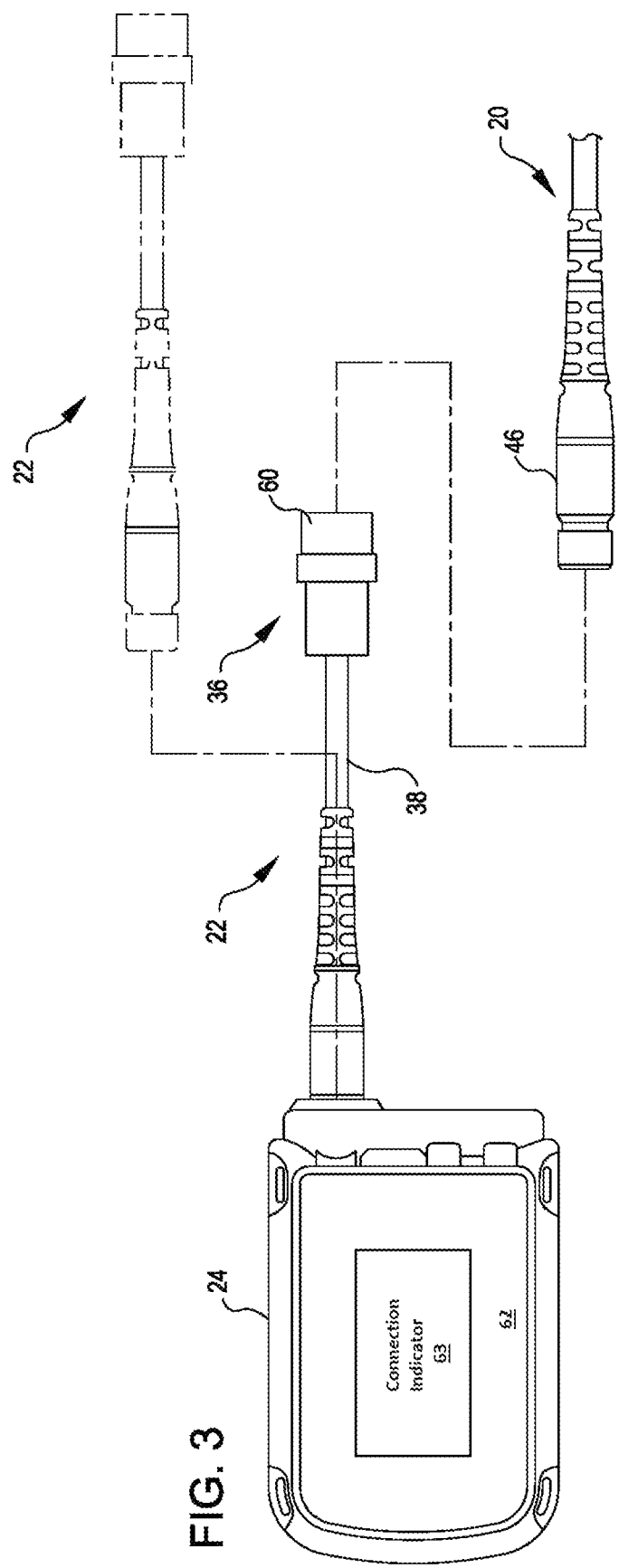
FIG. 3 is an exploded view illustrating connection of the external controller assembly with a distal driveline assembly in the blood circulation assist system of FIG. 1.

In the event of a fault in the external controller 24, it may be necessary to replace the faulted external controller to avoid potential detrimental prolonged disruption of operation of the blood pump 14. FIG. 3 is an exploded view illustrating the external controller 24, the external driveline assembly 22, and the intermediate driveline assembly 20. To facilitate replacement of the external controller 24 in the blood circulation assist system 10, in many embodiments, the external driveline assembly 22 can be connected to the intermediate driveline assembly 20 and disconnected from the intermediate driveline assembly 20 by the patient without the use of a tool. For example, in the illustrated embodiment, the external driveline distal connector 36 is configured as a female connector assembly and the intermediate driveline proximal connector 46 is configured as a male assembly that is inserted into the external driveline distal connector 36 by the patient. In the illustrated embodiment, the external driveline distal connector 36 includes a rotatable retention collar 60 that the patient can rotate, by hand without the use of a tool, between a connection orientation in which the retention collar 60 accommodates insertion of the intermediate driveline proximal connector 46 into the external driveline distal connector 36 and a retention orientation in which the retention collar 60 blocks disconnection of the intermediate driveline proximal connector 46 from the external driveline distal connector 36. In some embodiments, the retention collar 60 is rotatable by the patient through less than a full revolution (e.g., by a quarter turn, by a half turn) between the retention orientation and the connection orientation.

In some embodiments, the external controller 24 and the external driveline assembly 22 are adapted to detect whether the external driveline assembly 22 is connected to the intermediate driveline assembly 20 and display an indication on the external controller display 62 indicative of whether the external driveline assembly 22 is connected to the intermediate driveline assembly 20. For example, in some embodiments, the external driveline assembly 22 includes a first connection lead and a second connection lead. The second connection lead is electrically connected to the first connection lead while the external driveline distal connector 36 is connected to the distal driveline proximal connector 46. The second connection lead is electrically disconnected from the first connection lead while the external driveline distal connector 36 is not connected to the distal driveline proximal connector 46. The external controller 24 detects whether the external driveline distal connector 36 is connected to the distal driveline proximal connector 46 by detecting whether the second connection lead is electrically connected to the first connection lead. In many embodiments, the external controller 24 displays an indicator 63 on the external controller display 62 indicative of whether the external driveline distal connector 36 is connected to the distal driveline proximal connector 46. The displayed indicator 63 provides feedback to the patient as to whether the external driveline distal connector 36 is connected to the distal driveline proximal connector 46.

In many embodiments, the external driveline cable 38 has a length and a flexibility that enables the patient to position and/or orient the external driveline distal connector 36 to facilitate connection, by the patient, of the external driveline distal connector 36 to the intermediate driveline proximal connector 46 and disconnection, by the patient, of the external driveline distal connector 36 from the intermediate driveline proximal connector 46. For example, in some embodiments, the external driveline cable 38 has a length and a flexibility to accommodate the positioning of the external driveline distal connector 38, by the patient, for simultaneous viewing of the external driveline distal connector 36 and an external controller display 62 by the patient. In some embodiments, the length of the external driveline cable 38 and/or the overall length of the external driveline assembly 22 is from 5 inches to 9 inches.

Figure 4:
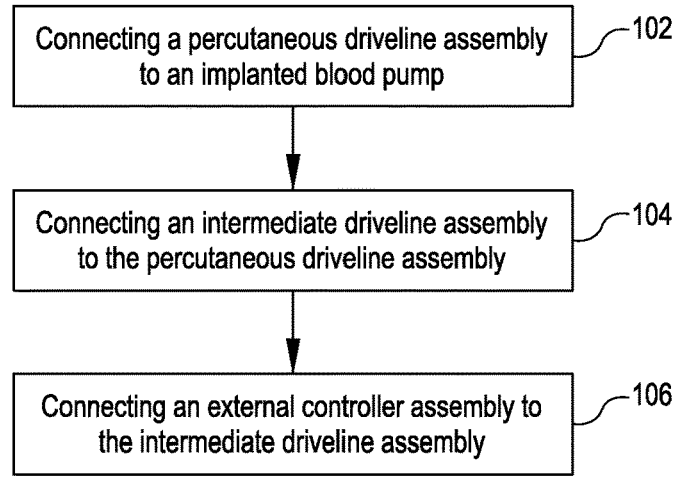
FIG. 4 is a simplified block diagram of a method of connecting an external controller to a blood pump implanted in a patient, in accordance with many embodiments.

FIG. 4 is a simplified block diagram of a method 100 of connecting an external controller to a blood pump implanted in a patient, in accordance with many embodiments. While the method 100 is described herein with reference to the blood circulation assist system 10, the method 100 can be practiced with respect to connecting any suitable external controller to any suitable medical device implanted in a patient.

The method 100 includes connecting a distal end of the percutaneous driveline assembly 18 to an implantable blood pump (act 102). For example, in the system 10, the percutaneous driveline distal connector 48 is connected to the percutaneous driveline connector 58. In many embodiments, the method 100 further includes securing the connection between the percutaneous driveline distal connector 48 and the percutaneous driveline connector 58 so as to prevent inadvertent disconnection thereof. For example, a suitable latching mechanism can be employed and reconfigured from a connection configuration accommodating the connection of the percutaneous driveline distal connector 48 to the percutaneous driveline connector 58 to a retention configuration that blocks disconnection of the percutaneous driveline distal connector 48 from the percutaneous driveline connector 58. In many embodiments, the method 100 further includes implanting a distal portion of the percutaneous driveline assembly 18 within the patient so that the skin-interface portion 54 of the percutaneous driveline cable 50 extends through an aperture through the skin of the patient with the skin-interface portion 54 interfacing with an edge of the skin at the aperture and the remaining proximal portion being disposed exterior to the patient.

The method 100 further includes connecting the intermediate driveline assembly 20 to the percutaneous driveline assembly 18 by connecting the intermediate driveline distal connector 42 to the percutaneous driveline proximal connector 52 (act 104). In many embodiments, the method 100 further includes securing the connection between the intermediate driveline distal connector 42 and the percutaneous driveline proximal connector 52 so as to prevent disconnection by the patient without the use of a specialized tool. For example, the connection between the intermediate driveline distal connector 42 and the percutaneous driveline proximal connector 52 can be secured by installing a retainer ring using a retainer ring plier so as to engage a respective retainer groove in each of the intermediate driveline distal connector 42 and the percutaneous driveline proximal connector 52.

The method 100 further includes connecting an external controller assembly to the intermediate driveline assembly 20 (act 106). For example, in the system 10, the external controller assembly includes the external driveline assembly 22 and the external controller 24. The external driveline assembly 22 is connected to the intermediate driveline assembly 20 by connecting the external driveline distal connector 36 to the intermediate driveline proximal connector 40. In many embodiments, the connection between the external driveline distal connector 36 and the intermediate driveline proximal connector 40 is patient-operable to accommodate connection and disconnection thereof, by the patient, to enable the patient to replace the external controller assembly with a replacement external controller assembly. In some embodiments, the method 100 further includes: (a) connecting the external driveline assembly 22 to the external controller 24 by connecting the external driveline proximal connector 40 to the external controller driveline connection port 56, and (b) securing the external driveline proximal connector 40 to the external controller driveline connection port 56 so as to prevent the patient from disconnecting the external driveline proximal connector 40 from the external controller driveline connection port 56 without the use of a key or a specialized tool. In alternate embodiments of the external controller assembly, the external driveline assembly 22 is integrally attached to the external controller 24 so that the external controller 24 does not include the external controller driveline connection port 56 and the external driveline assembly 22 does not include the external driveline proximal connector 40.

In many embodiments of the method, the external driveline cable 38 has a length and a flexibility that enables the patient to position and/or orient the external driveline distal connector 36 to facilitate connection, by the patient, of the external driveline distal connector 36 to the intermediate driveline proximal connector 46 and disconnection, by the patient, of the external driveline distal connector 36 from the intermediate driveline proximal connector 46. For example, in some embodiments, the external driveline cable 38 has a length and a flexibility to accommodate the positioning of the external driveline distal connector 36, by the patient, for simultaneous viewing of the external driveline distal connector 36 and the external controller display 62 by the patient. In some embodiments of the method, the length of the external driveline cable 38 is from 5 inches to 9 inches.

Figure 5:
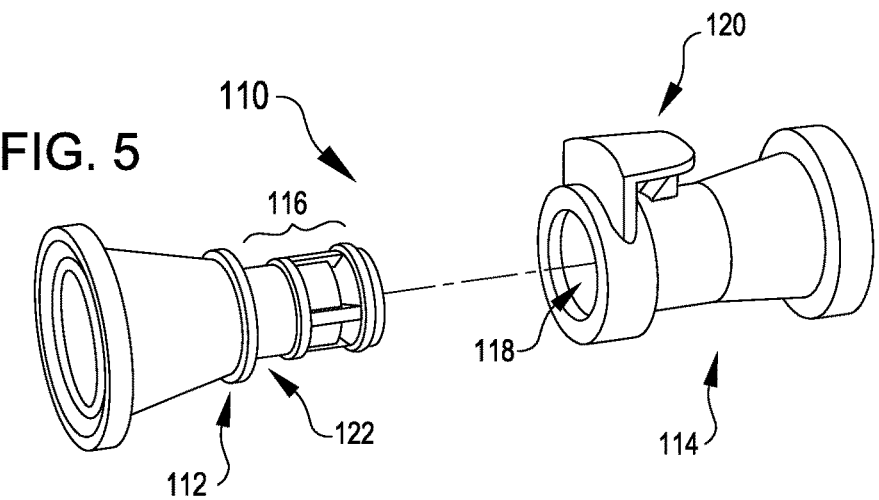
FIG. 5 shows an embodiment of a patient-operable connection assembly for connecting an external controller to a blood pump implanted in a patient and disconnecting the external controller to the blood pump.

FIG. 5 shows a patient-operable connection assembly 110 that can be employed in the patient-operable connection assembly 64 shown in FIG. 1. The connection assembly 110 includes a male connector component 112 and a female connector assembly 114. The female connector assembly 114 has a receptacle 118 and a latching mechanism 120. The male connector component 112 has an end portion 116 that has a retention groove 122. In some embodiments, the end portion 116 has one or more alignment features that engage complementarily-shaped alignment features of the female connector assembly 114 to ensure alignment with electrical contacts supported by the male connector component 112 with electrical contacts supported by the female connector assembly 114. The end portion 116 is adapted to be inserted into the receptacle 118 and retained in the receptacle 118 via engagement between the latching mechanism 120 and the retention groove 122. In some embodiments, the latching mechanism 120 is spring-biased towards a retention configuration in which the latching mechanism 120 is configured to retain the end portion 116 in the receptacle 118 via engagement with the retention groove 122. In such embodiments, insertion of the end portion 116 into the receptacle 118 induces a reconfiguration cycle in which interaction between the end portion 116 and the latching mechanism 120 causes the latching mechanism 120 to reconfigure so as to accommodate full insertion of the end portion 116 into the receptacle 118 to a depth where the retention groove 122 is positioned to be engaged by the latching mechanism 120. In such embodiments, once the end portion 116 is fully inserted into the receptacle 118, the latching mechanism 120 self-reconfigures back to the retention configuration, thereby engaging the retention groove 122 to prevent inadvertent decoupling of the male connector component 112 and the female connector assembly 114. In many embodiments, the latching mechanism 120 can be manually reconfigured by the patient from the retention configuration to a release configuration in which the male connector component 112 can be decoupled from the female connector assembly 114. For example, in many embodiments, the patient can push or pull on the latching mechanism 120 to reconfigure the latching mechanism 120 from the retention configuration to the release configuration to enable the patient to decouple the male connector component 112 from the female connector assembly 114. The male connector component 112 can be included in the intermediate driveline proximal connector 46. The female connector assembly 114 can be included in the external driveline distal connector 36.

Figure 6:
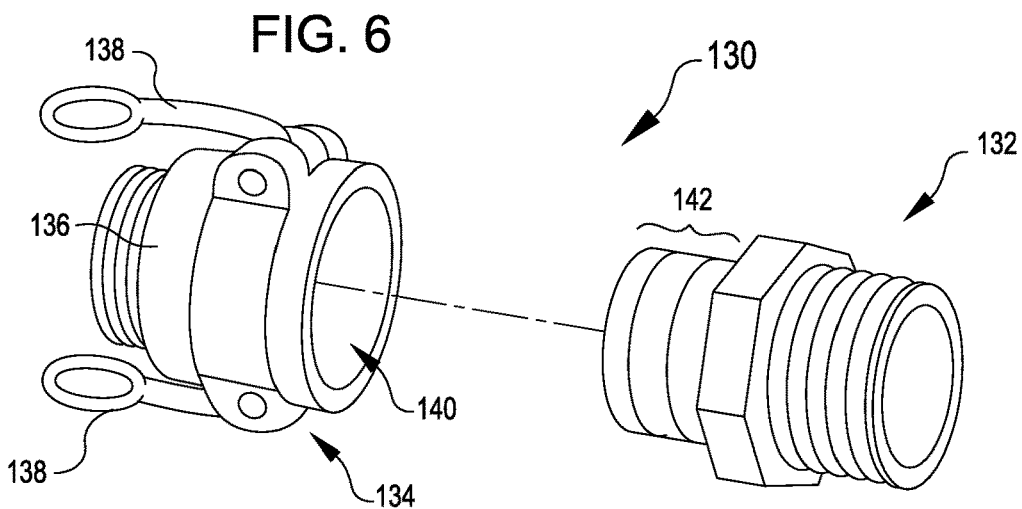
FIG. 6 shows another embodiment of a patient-operable connection assembly for connecting an external controller to a blood pump implanted in a patient and disconnecting the external controller to the blood pump.

FIG. 6 shows a patient-operable connection assembly 130 that can be employed in the patient-operable connection assembly 64 shown in FIG. 1. The connection assembly 130 includes a male connector component 132 and a female connector assembly 134. The female connector assembly 114 includes a base member 136 and latching members 138 that are pivotally mounted to the base member 136. The base member 136 defines a receptacle 140. The male connector component 132 has an end portion 142. In some embodiments, the end portion 142 has one or more alignment features that engage complementarily-shaped alignment features of the base member 136 to ensure alignment with electrical contacts supported by the male connector component 132 with electrical contacts supported by the female connector assembly 134. The end portion 142 is adapted to be inserted into the receptacle 140 and retained in the receptacle 140 via coupling of the latching members 138 with the male connector component 132. For example, in some embodiments, the male connector component 132 includes coupling features to which the latching members 138 can be selectively coupled with by the patient and decoupled from by the patient. The male connector component 132 can be included in the intermediate driveline proximal connector 46. The female connector assembly 134 can be included in the external driveline distal connector 36.

Figure 7:
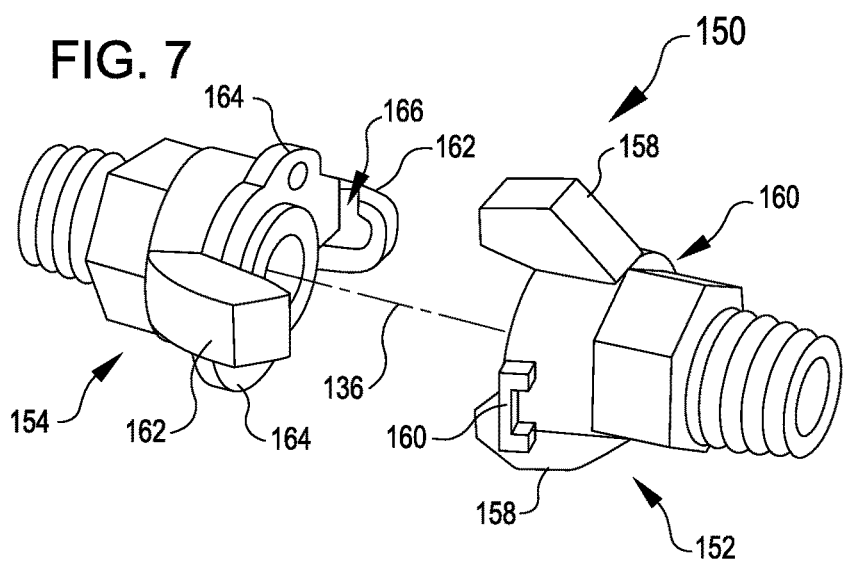
FIG. 7 shows another embodiment of a patient-operable connection assembly for connecting an external controller to a blood pump implanted in a patient and disconnecting the external controller to the blood pump.

FIG. 7 shows a patient-operable connection assembly 150 that can be employed in the patient-operable connection assembly 64 shown in FIG. 1. The connection assembly 150 includes a first connector component 152 and a second connector component 154. The first connector component 152 has retention features 158, 160. The second connector component 154 has retention features 162, 164. Each of the retention features 158 defines a slot 166 shaped to accommodate and engage a respective retention feature 164 when the connection assembly 150 is in a coupled configuration. Likewise, each of the retention features 162 defines a slot 166 shaped to accommodate and engage a respective retention feature 160 when the connection assembly 150 is in the coupled configuration. The connection assembly 150 is connectable by the patient via relative translation between the first connector component 152 and the second connector component 154 along a connection axis 156 to bring the first connector component 152 and the second connector component 154 into engagement in an intermediate configuration, followed by relative rotation between the first connector component 152 and the second connector component 154 around the connection axis 156 from the intermediate configuration into the coupled configuration. The connection assembly 150 can be disconnected by the patient via relative rotation between the first connector component 152 and the second connector component 154 around the connection axis 156 from the coupled configuration to the intermediate configuration, followed by relative translation between the first connector component 152 and the second connector component 154 along a connection axis 156 to separate the first connector component 152 and the second connector component 154. In some embodiments, the connection assembly 150 includes a patient-operable retention mechanism that prevents relative rotation between the first connector component 152 and the second connector component 154 in the coupled configuration of the connection assembly 150 absent reconfiguration of the retention mechanism by the patient into a release configuration that accommodates relative rotation between the first connector component 152 and the second connector component 154. The first connector component 152 can be included in the intermediate driveline proximal connector 46. The second connector component 154 can be included in the external driveline distal connector 36.

Figure 8:
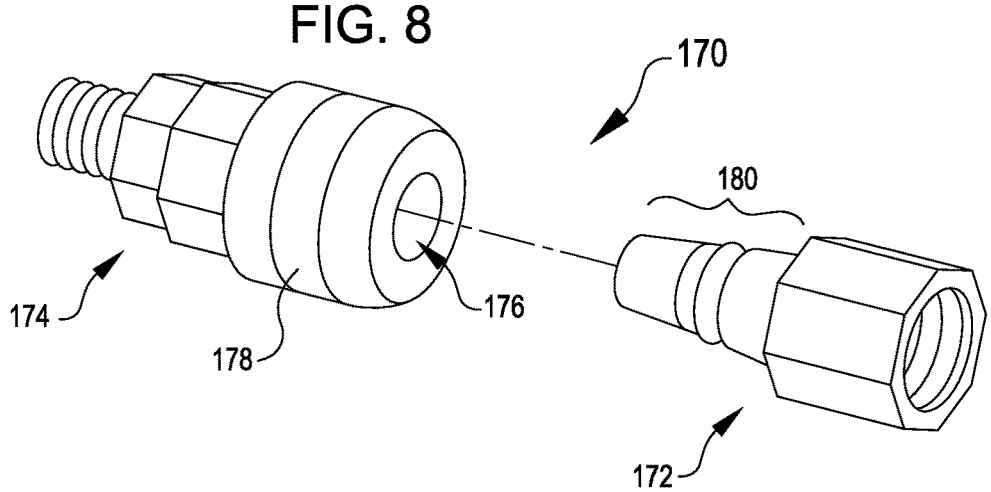
FIG. 8 shows another embodiment of a patient-operable connection assembly for connecting an external controller to a blood pump implanted in a patient and disconnecting the external controller to the blood pump.

FIG. 8 shows a patient-operable connection assembly 170 that can be employed in the patient-operable connection assembly 64 shown in FIG. 1. The connection assembly 170 includes a male connector component 172 and a female connector assembly 174. The female connector assembly 174 has a receptacle 176 and a translatable latching member 178. The male connector component 172 has an end portion 180. In some embodiments, the end portion 180 has one or more alignment features that engage complementarily-shaped alignment features of the female connector assembly 174 to ensure alignment with electrical contacts supported by the male connector component 172 with electrical contacts supported by the female connector assembly 174. The end portion 180 is adapted to be inserted into the receptacle 176 and retained in the receptacle 176 via engagement with the latching member 178. In some embodiments, the latching member 178 is spring-biased towards a retention configuration in which the female connector assembly 174 is configured to retain the end portion 180 in the receptacle 176. In some embodiments, insertion of the end portion 180 into the receptacle 176 induces a reconfiguration cycle in which interaction between the end portion 180 and the latching member 178 causes the latching member 178 to translate so as to accommodate full insertion of the end portion 180 into the receptacle 176. In such embodiments, once the end portion 180 is fully inserted into the receptacle 176, the latching member 178 translates back to the retention configuration, thereby engaging the end portion 180 to prevent inadvertent decoupling of the male connector component 172 and the female connector assembly 174. In many embodiments, the latching member 178 can be manually translated by the patient from the retention configuration to a release configuration in which the male connector component 172 can be decoupled from the female connector assembly 174. For example, in many embodiments, the patient can translate the latching member 178 to reconfigure the female connector assembly 174 from the retention configuration to the release configuration to enable the patient to decouple the male connector component 172 from the female connector assembly 174. The male connector component 172 can be included in the intermediate driveline proximal connector 46. The female connector assembly 174 can be included in the external driveline distal connector 36.

Figure 9:
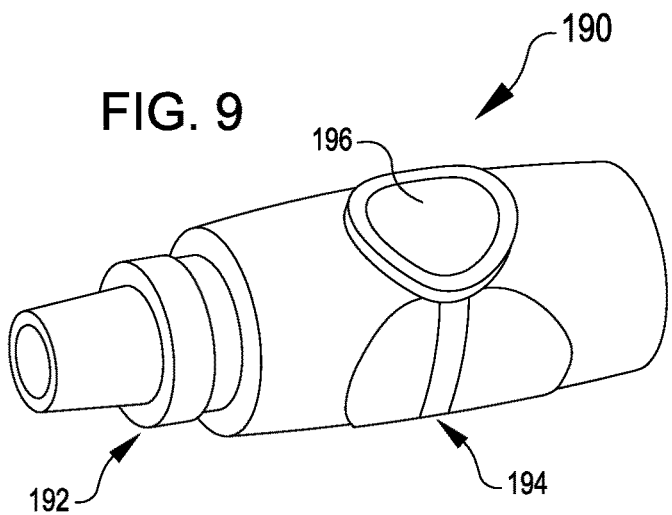
FIG. 9 shows another embodiment of a patient-operable connection assembly for connecting an external controller to a blood pump implanted in a patient and disconnecting the external controller to the blood pump.

FIG. 9 shows a patient-operable connection assembly 190 that can be employed in the patient-operable connection assembly 64 shown in FIG. 1. The connection assembly 190 includes a male connector component 192 and a female connector assembly 194. The female connector assembly 194 has a latching mechanism that includes a patient-operable release button 196 that can be pressed by the patient to enable decoupling of the male connector component 192 from the female connector assembly 194. In many embodiments, the connection assembly 190 is configured similar to the connection assembly 110 with respect to the ability of the latching mechanism to accommodate insertion of the male connector component 192 into the female connector assembly 194 and have the latching mechanism automatically reconfigure into the retention configuration upon full insertion of the male connector component 192 into the female connector assembly 194. In many embodiments, the release button 196 is recessed relative to the surrounding adjacent exterior surface of the female connector assembly 194 to prevent inadvertent pressing of the release button 196. The male connector component 192 can be included in the intermediate driveline proximal connector 46. The female connector assembly 194 can be included in the external driveline distal connector 36.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A blood circulation assist system, comprising:
an implantable blood pump;

an external controller via which power to operate the implantable blood pump is supplied to the implantable blood pump, the external controller including an external controller display viewable by a patient in which the implantable blood pump is implanted;

a distal driveline assembly comprising a percutaneous cable connected to the implantable blood pump and a distal driveline proximal connector electrically coupled with the percutaneous cable, the percutaneous cable having a skin-interface segment adapted to extend through a skin of a patient, wherein the distal driveline assembly has a flexibility and an exterior length from the skin-interface segment to the distal driveline proximal connector that accommodates positioning of the distal driveline proximal connector, by the patient, between the external controller display and an eye of the patient, and wherein the exterior length of the distal driveline assembly is from 3.0 inches to 7.0 inches; and an external driveline assembly comprising an external driveline cable and an external driveline distal connector, the external driveline cable being connected to the external driveline distal connector and the external controller, the external driveline cable accommodating positioning of the external driveline distal connector, by the patient, for simultaneous viewing of the external driveline distal connector and the external controller display by the patient, wherein the external driveline distal connector is adapted to be connected to the distal driveline proximal connector by the patient, and wherein the external driveline distal connector is adapted to be disconnected from the distal driveline proximal connector by the patient, wherein the external controller and the external driveline assembly are adapted to detect whether the external driveline assembly is connected to the distal driveline assembly and display an indication on the external controller display indicative of whether the external driveline assembly is connected to the distal driveline assembly.

2. The blood circulation assist system of claim 1, wherein the external driveline cable has a length and a flexibility to accommodate the positioning of the external driveline distal connector, by the patient, for simultaneous viewing of the external driveline distal connector and the external controller display by the patient.

3. The blood circulation assist system of claim 2, wherein the length of the external driveline cable is from 5 inches to 9 inches.

4. The blood circulation assist system of claim 3, wherein:
the external controller comprises an external driveline connection port;
the external driveline assembly comprises an external driveline proximal connector that is connects the external driveline cable to the external driveline connection port; and
the external controller comprises an external driveline latching mechanism that prevents the patient from disconnecting the external driveline proximal connector from the external driveline connection port without use of a tool.

5. The blood circulation assist system of claim 1, wherein:
the external driveline assembly comprises a first connection lead and a second connection lead;
the second connection lead is electrically connected to the first connection lead while the external driveline distal connector is connected to the distal driveline proximal connector;
the second connection lead is electrically disconnected from the first connection lead while the external driveline distal connector is not connected to the distal driveline proximal connector; and
the external controller detects whether the external driveline distal connector is connected to the distal driveline proximal connector by detecting whether the second connection lead is electrically connected to the first connection lead.

6. The blood circulation assist system of claim 1, wherein the distal driveline assembly comprises:
an intermediate driveline assembly that includes the distal driveline proximal connector, an intermediate driveline cable, and an intermediate driveline distal connector; the intermediate driveline cable connecting the distal driveline proximal connector to the intermediate driveline distal connector; and
a percutaneous driveline assembly that includes a percutaneous driveline proximal connector and the percutaneous cable, the percutaneous driveline proximal connector being connectable to the intermediate driveline distal connector.

7. The blood circulation assist system of claim 6, wherein the percutaneous driveline proximal connector and the intermediate driveline distal connector are adapted to be connected so that the patient cannot disconnect the intermediate driveline distal connector and the percutaneous driveline proximal connector without use of a tool.

8. The blood circulation assist system of claim 7, further comprising an intermediate driveline latching mechanism that prevents disconnection of the percutaneous driveline proximal connector and the intermediate driveline distal connector without use of a specialized tool.

9. The blood circulation assist system of claim 1, wherein:
the external driveline distal connector and the distal driveline proximal connector are included in a patient-operable connection assembly;
the patient-operable connection assembly comprises a latching mechanism having a retention configuration and a release configuration;
the latching mechanism blocks decoupling of the external driveline distal connector from the distal driveline proximal connector in the retention configuration;
the latching mechanism accommodates decoupling of the external driveline distal connector from the distal driveline proximal connector in the release configuration; and
the latching mechanism is reconfigurable by the patient from the retention configuration to the release configuration.

10. The blood circulation assist system of claim 9, wherein the latching mechanism is reconfigured from the retention configuration to the release configuration via relative rotation of the external driveline distal connector and the distal driveline proximal connector by the patient.

11. The blood circulation assist system of claim 9, wherein the latching mechanism comprises a latching member that is operated by the patient to reconfigure the latching mechanism from the retention configuration to the release configuration.

12. A method of connecting an external controller to a blood pump implanted in a patient, the method comprising:
connecting a distal end of a percutaneous driveline assembly to the blood pump, the percutaneous driveline assembly comprising a percutaneous driveline cable and a percutaneous driveline proximal connector, the percutaneous driveline cable extending between the blood pump and the percutaneous driveline proximal connector, the percutaneous driveline cable having a skin-interface segment that extends through a skin of the patient;

connecting an intermediate driveline assembly to the percutaneous driveline assembly by connecting an intermediate driveline distal connector of the intermediate driveline assembly to the percutaneous driveline proximal connector, the intermediate driveline assembly comprising an intermediate driveline proximal connector and an intermediate driveline cable connecting the intermediate driveline distal connector and the intermediate driveline proximal connector;

connecting an external controller assembly to the intermediate driveline assembly, the external controller assembly comprising an external driveline assembly and an external controller via which power is supplied to the blood pump, the external driveline assembly comprising an external driveline cable and an external driveline distal connector, the external driveline cable connecting the external driveline distal connector and the external controller, the external controller comprising an external controller display viewable by the patient, the external driveline cable and the intermediate driveline assembly accommodating positioning of the external driveline distal connector and the intermediate driveline proximal connector, by the patient, for simultaneous viewing and disconnection of the external driveline distal connector and the intermediate driveline proximal connector and the external controller display by the patient;

detecting whether the external driveline distal connector is connected to the intermediate driveline proximal connector; and displaying an indication on the external controller display indicative of whether the external driveline assembly is connected to the intermediate driveline assembly.

13. The method of claim 12, further comprising securing the intermediate driveline distal connector to the percutaneous driveline proximal connector so as to prevent the patient from disconnecting the intermediate driveline distal connector from the percutaneous driveline proximal connector without use of a tool.

14. The method of claim 12, further comprising:
connecting the external driveline assembly to the external controller by connecting an external driveline proximal connector of the external driveline assembly to an external driveline connection port of the external controller; and
securing the external driveline proximal connector to the external driveline connection port so as to prevent the patient from disconnecting the external driveline proximal connector from the external driveline connection port without use of a tool.

15. The method of claim 12, wherein:
the external driveline cable has a length from 5 inches to 9 inches; and
a length of the intermediate driveline assembly and the percutaneous driveline assembly to the skin-interface segment is from 3.0 inches to 7.0 inches.

16. An external controller assembly for an implanted blood pump assembly, the external controller assembly comprising:
an external controller via which power is supplied to the implanted blood pump assembly, the external controller including an external controller display viewable by a patient in which the implanted blood pump assembly is implanted;
an external driveline assembly comprising an external driveline cable and an external driveline distal connector, the external driveline cable being connected to the external driveline distal connector and the external controller; and
an intermediate driveline assembly comprising an intermediate driveline cable, an intermediate driveline proximal connector, and an intermediate driveline distal connector; wherein the intermediate driveline proximal connector is adapted to be connected to the external driveline distal connector by the patient, wherein the intermediate driveline proximal connector is adapted to be disconnected to the external driveline distal connector by the patient, wherein the intermediate driveline distal connector is adapted to be connected to a percutaneous cable proximal connector of a percutaneous driveline assembly connected to the implanted blood pump assembly, wherein the intermediate driveline assembly and the percutaneous driveline assembly have a flexibility and an exterior length from a skin-interface segment of the percutaneous driveline assembly to the intermediate driveline proximal connector that accommodates positioning of the intermediate driveline proximal connector, by the patient, between the external controller display and an eye of the patient, and wherein a length of the intermediate driveline assembly and the percutaneous driveline assembly to the skin-interface segment is from 3.0 inches to 7.0 inches, wherein the external controller and the external driveline assembly are adapted to detect whether the external driveline assembly is connected to the intermediate driveline assembly and display an indication on the external controller display indicative of whether the external driveline assembly is connected to the intermediate driveline assembly.

17. The external controller assembly of claim 16, wherein the external driveline cable has a length and a flexibility to accommodate the positioning of the external driveline distal connector, by the patient, for simultaneous viewing of the external driveline distal connector and the external controller display by the patient.

18. The external controller assembly of claim 17, wherein the length of the external driveline cable is from 5 inches to 9 inches.

19. The external controller assembly of claim 18, wherein:
the external controller comprises an external driveline connection port;
the external driveline assembly comprises an external driveline proximal connector that connects the external driveline cable to the external driveline connection port; and
the external controller comprises an external driveline latching mechanism that prevents the patient from disconnecting the external driveline proximal connector from the external driveline connection port without use of a tool.

20. The external controller assembly of claim 16, wherein:
the external driveline assembly comprises a first connection lead and a second connection lead;

the second connection lead is electrically connected to the first connection lead while the external driveline distal connector is connected to the intermediate driveline proximal connector;

the second connection lead is electrically disconnected from the first connection lead while the external driveline distal connector is not connected to the intermediate driveline proximal connector; and the external controller detects whether the external driveline distal connector is connected to the intermediate driveline proximal connector by detecting whether the second connection lead is electrically connected to the first connection lead.

\* \* \* \* \*